(12) United States Patent
Patel et al.

(10) Patent No.: US 9,120,298 B2
(45) Date of Patent: Sep. 1, 2015

(54) METHOD OF CONTINUOUSLY MANUFACTURING MICROFLUIDIC CHIPS WITH BOPET FILM FOR A MICROFLUIDIC DEVICE AND MICROFLUIDIC CHIPS WITH BOPET FILM

(71) Applicants: Tej Patel, San Diego, CA (US); Ryan Revilla, Downey, CA (US); Matthew D'Ooge, Carlsbad, CA (US)

(72) Inventors: Tej Patel, San Diego, CA (US); Ryan Revilla, Downey, CA (US); Matthew D'Ooge, Carlsbad, CA (US)

(73) Assignee: FluxErgy, LLC, San Diego, CA (US)

( * ) Notice: Subject to any disclaimer, the term of this patent is extended or adjusted under 35 U.S.C. 154(b) by 0 days.

(21) Appl. No.: 14/028,106

(22) Filed: Sep. 16, 2013

(65) Prior Publication Data

US 2015/0078971 A1 Mar. 19, 2015

(51) Int. Cl.
| | | |
|---|---|---|
| *B32B 37/00* | (2006.01) | |
| *B32B 37/02* | (2006.01) | |
| *B32B 37/14* | (2006.01) | |
| *B32B 37/18* | (2006.01) | |
| *B01L 3/00* | (2006.01) | |
| *B81C 3/00* | (2006.01) | |
| *B32B 37/12* | (2006.01) | |
| *B81B 1/00* | (2006.01) | |
| *G01N 27/447* | (2006.01) | |
| *G01N 35/00* | (2006.01) | |

(52) U.S. Cl.
CPC ....... *B32B 37/1284* (2013.01); *B01L 3/502707* (2013.01); *B32B 37/02* (2013.01); *B81C 3/001* (2013.01); *B01J 2219/00783* (2013.01); *B01L 2200/02* (2013.01); *B01L 2300/0816* (2013.01); *B01L 2300/0887* (2013.01); *B01L 2300/12* (2013.01); *B01L 2300/16* (2013.01); *B32B 2037/1253* (2013.01); *B32B 2307/518* (2013.01); *B32B 2310/0831* (2013.01); *B32B 2310/0843* (2013.01); *B32B 2315/08* (2013.01); *B32B 2367/00* (2013.01); *B81C 2201/019* (2013.01); *G01N 27/44791* (2013.01); *G01N 2035/00158* (2013.01)

(58) Field of Classification Search
None
See application file for complete search history.

(56) References Cited

U.S. PATENT DOCUMENTS

| | | | | |
|---|---|---|---|---|
| 5,376,252 | A * | 12/1994 | Ekstrom et al. | 204/603 |
| 6,752,966 | B1 * | 6/2004 | Chazan | 422/503 |
| 2009/0068760 | A1 * | 3/2009 | Nelson et al. | 436/518 |
| 2010/0233038 | A1 * | 9/2010 | Park et al. | 422/103 |
| 2010/0323924 | A1 * | 12/2010 | Li et al. | 506/33 |
| 2012/0235252 | A1 * | 9/2012 | Pinter | 257/415 |

\* cited by examiner

*Primary Examiner* — Jennifer Wecker
(74) *Attorney, Agent, or Firm* — Law Offices of S.J. Christine Yang

(57) ABSTRACT

A microfluidic chip includes a thin biaxially-oriented polyethylene terephthalate ("BoPET") film and a micro-channel in the BoPET film. A method for manufacturing a microfluidic chip includes coating UV epoxy on a first side of a BoPET film, placing the BoPET film on a first substrate with the first side facing the first substrate, curing the UV epoxy on the first side of the BoPET film to attach the BoPET film on the first substrate; forming at least one microfluidic pathway in the BoPET film, coating UV epoxy on a first side of a second substrate, placing the second substrate on the BoPET film with the first side of the second substrate facing a second side of the BoPET film, and curing the UV epoxy on the first side of the second substrate to attach the BoPET film to the second substrate. The microfluidic chip may be a multi-layered chip.

20 Claims, 11 Drawing Sheets

Deposit photoresist on Si Wafer
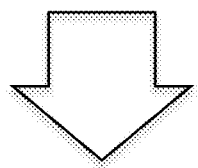
UV exposition over a mask
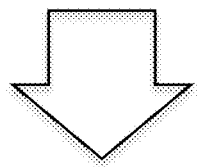
Photoresist Photopatterned
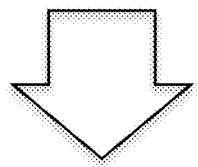
Develop the Mold
FIGURE 1
(Related Art)

Pour PDMS (liquid) and crosslinking agent into the mold
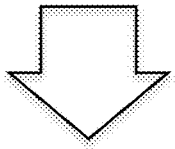
Place into a furnace to harden PDMS
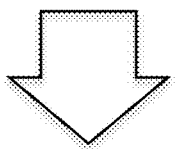
Release the PDMS block with microchannels
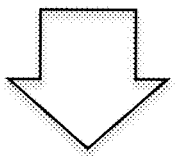
Form inlet and outlet in the microchannel using a needle
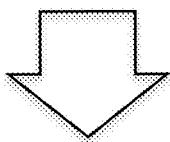
Bond a glass slide onto the face of the PDMS block
FIGURE 3
(Related Art)

Coat BoPET or Mylar film with UV epoxy

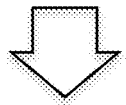

Place BoPET or Mylar film on a glass slide or PET block

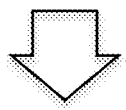

Cure the UV epoxy to bond the BoPET or Mylar film to the glass slide or PET block

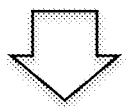

Ablate microchannel and inlet/outlet using a laser

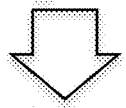

Place a second glass slide or PET block on the BoPET or Mylar film with microchannel (one side of the second glass slide is coated with UV expoxy)

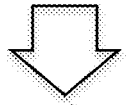

Cure the UV exposy to bond the second glass slide or PET block and the BoPET or Mylar film

FIGURE 5

METHOD OF CONTINUOUSLY MANUFACTURING MICROFLUIDIC CHIPS WITH BOPET FILM FOR A MICROFLUIDIC DEVICE AND MICROFLUIDIC CHIPS WITH BOPET FILM

BACKGROUND OF THE INVENTION

1. Field of the Invention

The present invention relates generally to a method of manufacturing microfluidic chips for handling fluid samples on a microfluidic level, and, more specifically, to a method of continuously manufacturing microfluidic chips for handling fluid samples on a microfluidic level and microfluidic chips manufactured using the same. The manufactured microfluidic chips can be used to perform analysis, for example, polymerase chain reaction (PCR) analysis.

2. Discussion of the Related Art

Microfluidics refers to the technology that relates to the flow of liquid in channels of micrometer size. At least one dimension of the channel is of the order of a micrometer or tens of micrometers to be considered as microfluidics. Microfluidics can be used in medicine or cell biology researches.

Microfluidic devices are useful for manipulating or analyzing micro-sized fluid samples, with the fluid samples typically in extremely small volumes down to less than pico liters. When manipulating or analyzing fluid samples, fluids are continuously flowed onto microfluidic chips or pumped onto microfluidic chips in doses.

A microfluidic chip includes at least one channel in a chip-shaped substrate. During manipulation or analysis of the fluid, the fluid is introduced into the channel. Typically, one end of the channel is an inlet through which the fluid enters, and another end of the channel is an outlet through which the fluid exits. Additionally, one or more valves can be along the channel pathway to control the movement of the fluid. For example, a microfluidic chip can include various functional units performing predetermined functions using the fluid and the valve(s) can limit or hold the fluid within a particular unit for a predetermined manner prior to the fluid being injected to another particular unit.

Presently, microfluidic chips have micro-channels are manufactured in batches. First, a design channel is made. Then, a mold reflecting the channel design is made. Using the mold, the channel design in imprinted in PolyDiMethyiSiloxane ("PDMS") block, and a glass slide is bonded over the micro-channels and on the PDMS block to seal the micro-channels. Such microfluidic chip is made one at the time to replicate the channel design in the mold.

FIG. 1 is a flow illustration of steps for manufacturing a microfluidic chip mold according to the related art, and FIGS. 2A-2D are perspective views of the manufacturing of a microfluidic chip mold according to the related art. The manufacturing of a microfluidic chip according to the related art takes a channel design and duplicates the channel design onto a photomask 10.

As shown in FIG. 1 and FIG. 2A, a photoresist 22 is deposited onto a semiconductor wafer 20. As shown in FIGS. 1 and 2B, the photomask 10 that reflects the channel design 12 is then placed over the wafer 20, and the wafer 20 with the mask 10 undergoes UV exposition to cure the photoresist 22. Then, as shown in FIGS. 1 and 2C, the wafer 20 with the cured photoresist 22' is developed. The 'negative' image of a channel according to the channel design is etched away from the semiconductor wafer 20. As shown in FIGS. 1 and 2D, after all residual photoresist are removed, the resulting wafer becomes a mold 20' that provides the channel according to the channel design 12'.

FIG. 3 is a flow illustration of steps for manufacturing a microfluidic chip according to the related art, and FIG. 4 reflects perspective views of the manufacturing of a microfluidic chip according to the related art. The manufacturing of a microfluidic chip according to the related art takes the mold and makes microfluidic chips in batches.

As shown in FIG. 4, the mold 20' may first be clean. As shown in FIGS. 3 and 4, PDMS in liquid form 30 is poured onto the mold 20'. Liquid PDMS 30 may be mixed with crosslinking agent. The mold 20' with liquid PDMS 30 is then placed into a furnace to harden PDMS 30. As shown in FIGS. 3 and 4, as PDMS is hardened, the hardened PDMS block 30' duplicates the micro-channel 12" according to the channel design. The PDMS block 30' then may be separated from the mold 20'. To allow injection of fluid into the micro-channel 12"(which will subsequently be sealed), inlet or outlet is then made in the PDMS block 30' by drilling into the PDMS block 30' using a needle, as shown in FIGS. 3 and 4.

Then, as shown in FIGS. 3 and 4, the face of the PDMS block 30' with micro-channels and a glass slide 32 are treated with plasma. Due to the plasma treatment, the PDMS block 30' and the glass slide 32 can bond with one another and close the chip, as shown in FIGS. 3 and 4.

To manufacture a microfluidic chip according to the related art involves first manufacturing a master mold and then, separately duplicating channel designs onto PDMS. The related art method would require manufacturing microfluidic chips in batches, and the output rate based on this related art method is limited by the number of master molds. Thus, there continues to exist a need for developing a method of manufacturing microfluidic chips that manufactures microfluidic chips continuously, and that is quick, simple, reliable and cost effective.

Therefore, what is needed is a method of manufacturing that can continuously, reliably and quickly form micro-channels in chips, so that it is more cost effective to manufacture microfluidic chips. Also needed is a method of manufacturing microfluidic chips that is more flexible in adopting different micro-channel designs and can quickly adopt a different micro-channel design in a consistently controlled manner.

SUMMARY OF THE INVENTION

Accordingly, embodiments of the invention are directed to a method of continuously manufacturing microfluidic chips for handling fluid samples on a microfluidic level and microfluidic chips that can substantially obviate one or more of the problems due to limitations and disadvantages of the related art.

An object of embodiments of the invention is to provide a method of manufacturing microfluidic chips that can continuously form micro-channels in chips.

Another object of embodiments of the invention is to provide microfluidic chips that are manufactured by using a method that can continuously form micro-channels in chips.

An object of embodiments of the invention is to provide a method of manufacturing microfluidic chips that can reliably and quickly form micro-channels in chips.

Another object of embodiments of the invention is to provide microfluidic chips manufactured using a method that can reliably and quickly form micro-channels in chips.

An object of embodiments of the invention is to provide a method of manufacturing microfluidic chips that can dynamically adopt micro-channel designs for microfluidic chips.

Another object of embodiments of the invention is to provide microfluidic chips manufactured using a method that can dynamically adopt micro-channel designs.

Another object of embodiments of the invention is to provide microfluidic chips having micro-channels in a thin biaxially-oriented polyethylene terephthalate ("BoPET") film. The PET film may be Mylar or another transparent, stable, and electrical insulative film.

Additional features and advantages of embodiments of the invention will be set forth in the description which follows, and in part will be apparent from the description, or may be learned by practice of embodiments of the invention. The objectives and other advantages of the embodiments of the invention will be realized and attained by the structure particularly pointed out in the written description and claims hereof as well as the appended drawings.

To achieve these and other advantages and in accordance with the purpose of embodiments of the invention, as embodied and broadly described, a method for manufacturing a device according to an embodiment of the present invention includes coating UV epoxy on a first side of a BoPET film, placing the BoPET film on a first substrate with the first side facing the first substrate, curing the UV epoxy on the first side of the BoPET film to attach the BoPET film on the first substrate, forming at least one microfluidic pathway in the BoPET film, coating UV epoxy on a first side of a second substrate, placing the second substrate on the BoPET film with the first side of the second substrate facing a second side of the BoPET film, and curing the UV epoxy on the first side of the second substrate to attach the BoPET film to the second substrate.

In accordance with another embodiment of the invention, as embodied and broadly described, there is a method for manufacturing a device that includes coating UV epoxy on a first side of a BoPET film, placing the BoPET film on a first substrate with the first side facing the first substrate, curing the UV epoxy on the first side of the BoPET film to attach the BoPET film on the first substrate, forming at least one microfluidic pathway in the BoPET film, coating UV epoxy on a first side of a second substrate, placing the second substrate on the BoPET film with the first side of the second substrate facing a second side of the BoPET film, curing the UV epoxy on the first side of the second substrate to attach the BoPET film to the second substrate, coating UV epoxy on a first side of a second BoPET film, placing the second BoPET film on the second substrate with the first side of the second BoPET film facing the second substrate, curing the UV epoxy on the first side of the second BoPET film to attach the second BoPET film on the second substrate, forming at least one microfluidic pathway in the second BoPET film, coating UV epoxy on a first side of a third substrate, placing the third substrate on the second BoPET film with the first side of the second substrate facing a second side of the BoPET film, and curing the UV epoxy on the first side of the third substrate to attach the second BoPET film to the third substrate.

In accordance with another embodiment of the invention, as embodied and broadly described, a microfluidic chip is manufactured by using the method that includes coating UV epoxy on a first side of a BoPET film, placing the BoPET film on a first substrate with the first side facing the first substrate, curing the UV epoxy on the first side of the BoPET film to attach the BoPET film on the first substrate, forming at least one microfluidic pathway in the BoPET film, coating UV epoxy on a first side of a second substrate, placing the second substrate on the BoPET film with the first side of the second substrate facing a second side of the BoPET film, and curing the UV epoxy on the first side of the second substrate to attach the BoPET film to the second substrate.

In accordance with another embodiment of the invention, as embodied and broadly described, a microfluidic chip includes a first substrate, a BoPET film bonded on the first substrate, wherein a least one microfluidic pathway in the BoPET film, a second substrate bonded on the BoPET film.

It is to be understood that both the foregoing general description and the following detailed description are exemplary and explanatory and are intended to provide further explanation of embodiments of the invention as claimed.

BRIEF DESCRIPTION OF THE DRAWINGS

The accompanying drawings, which are included to provide a further understanding of embodiments of the invention and are incorporated in and constitute a part of this specification, illustrate embodiments of the invention and together with the description serve to explain the principles of embodiments of the invention.

FIG. 1 is a flow illustration of steps for manufacturing a microfluidic chip mold according to the related art.

FIG. 3 is a flow illustration of steps for manufacturing a microfluidic chip according to the related art.

FIG. 5 is a flow illustration of steps for manufacturing microfluidic chips according to an embodiment of the present invention.

DETAILED DESCRIPTION OF THE PREFERRED EMBODIMENTS

Reference will now be made in detail to the preferred embodiments of the invention, examples of which are illustrated in the accompanying drawings.

FIG. 5 is a flow illustration of steps for manufacturing microfluidic chips according to an embodiment of the present invention. As shown in FIG. 5, the method for manufacturing microfluidic chips includes coating a thin transparent polyester film with UV epoxy. Preferably, a thin biaxially-oriented polyethylene terephthalate ("BoPET") film is coated with UV epoxy. BoPET film may be Mylar, Melinex or Hostaphan. Alternatively, a transparent, stable and electrical insulative polyester film with high tensile strength may be used.

After the polyester film is coated with UV epoxy, the film is placed on a glass slide or PET block and undergoes UV exposure to cure the epoxy. Thereby, the film is bonded on the glass slide or PET block.

After the film is bonded onto the glass slide or PET block, micro-channel(s) is made by ablating the film using laser beams. In addition, an inlet or an outlet is also made by further ablating through-holes into the glass slide or PET block. After the completion of ablating the film, a second glass slide or PET block is placed over the film to seal the micro-channel(s).

In particular, the second glass slide or PET block is coated with UV epoxy. After the second glass slide or PET block is coated with UV epoxy, the second glass slide or PET is placed on the film with micro-channel(s) and undergoes UV exposure to cure the epoxy. Thereby, the second glass slide or PET block is bonded on the film with micro-channel(s).

Therefore, the method for manufacturing microfluidic chips according to an embodiment of the present invention does not involve a master mold. Further, the method for manufacturing microfluidic chips according to an embodiment of the present invention can be performed in a continuous manner. For example, each step may be performed at different stations of a manufacturing production line and a first station may only perform the step of coating UV epoxy on a thin film piece, and each thin film is then passed onto the next station after being coated by the first station.

Figure 2A:
FIGS. 2A-2D are perspective views of the manufacturing of a microfluidic chip mold according to the related art.
Figure 2B:
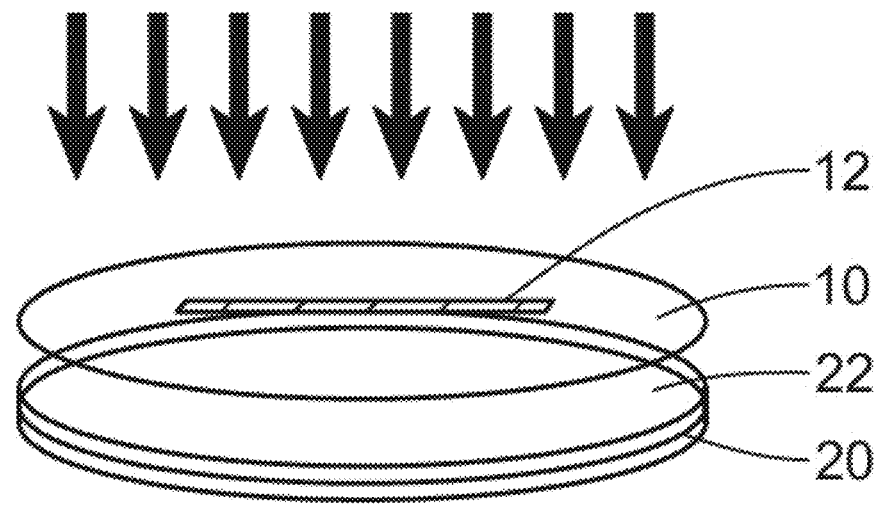
Figure 2C:
Figure 2D:
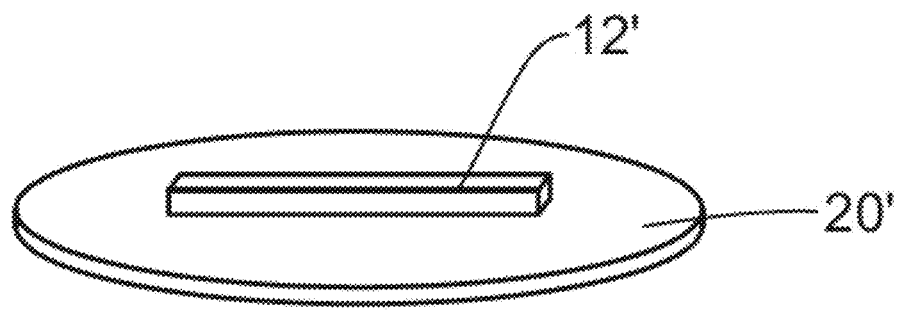
Figure 4:
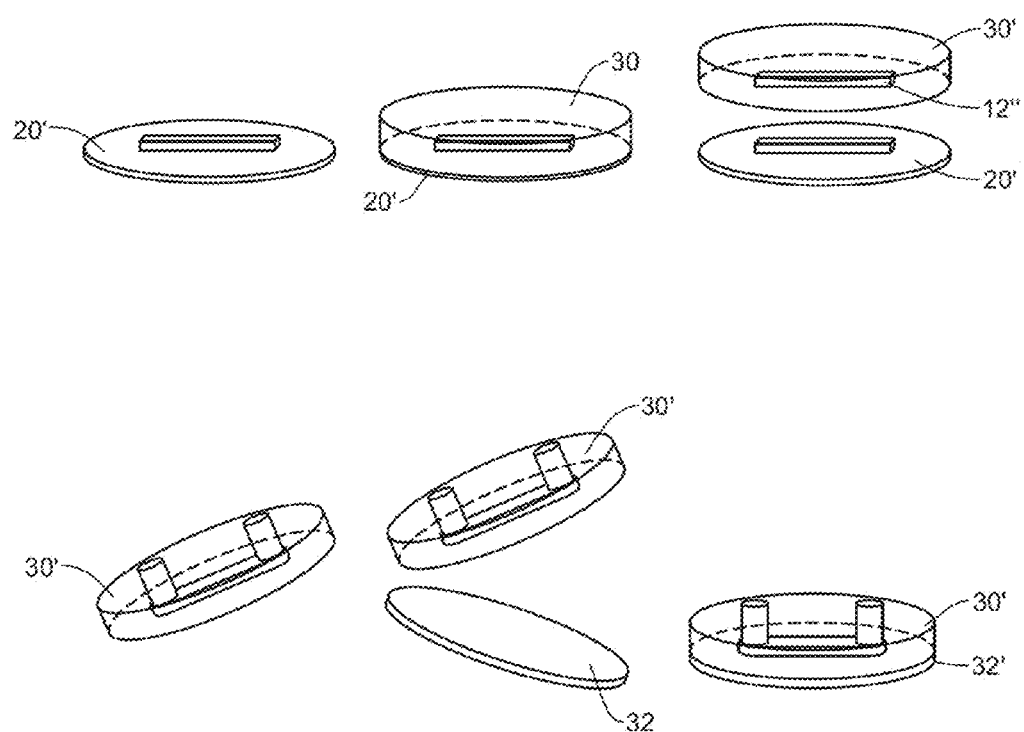
FIG. 4 reflects perspective views of the manufacturing of a microfluidic chip according to the related art.
Figure 6A:
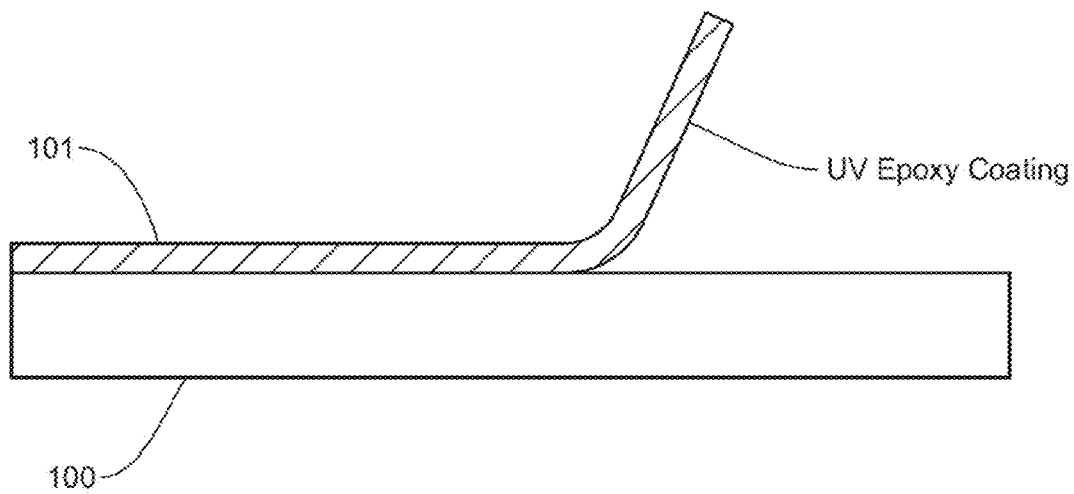
FIGS. 6A-6F are illustration of the manufacturing of microfluidic chips according to an embodiment of the present invention.

FIGS. 6A-6G are illustration of the manufacturing of microfluidic chips according to an embodiment of the present invention. As shown in FIG. 6A, a first surface of a thin transparent polyester film 101 is coated with UV epoxy. Preferably, the thin transparent polyester film 101 is a thin biaxially-oriented polyethylene terephthalate ("BoPET") film. BoPET film may be Mylar, Melinex or Hostaphan. Alternatively, the thin transparent polyester film 101 is a transparent, stable and electrical insulative polyester film with high tensile strength may be used. The thin transparent polyester film 101 is placed on a first glass slide or PET block 100. The first glass slide or PET block 100 may first undergo a cleaning step (which is not shown).

Figure 6B:
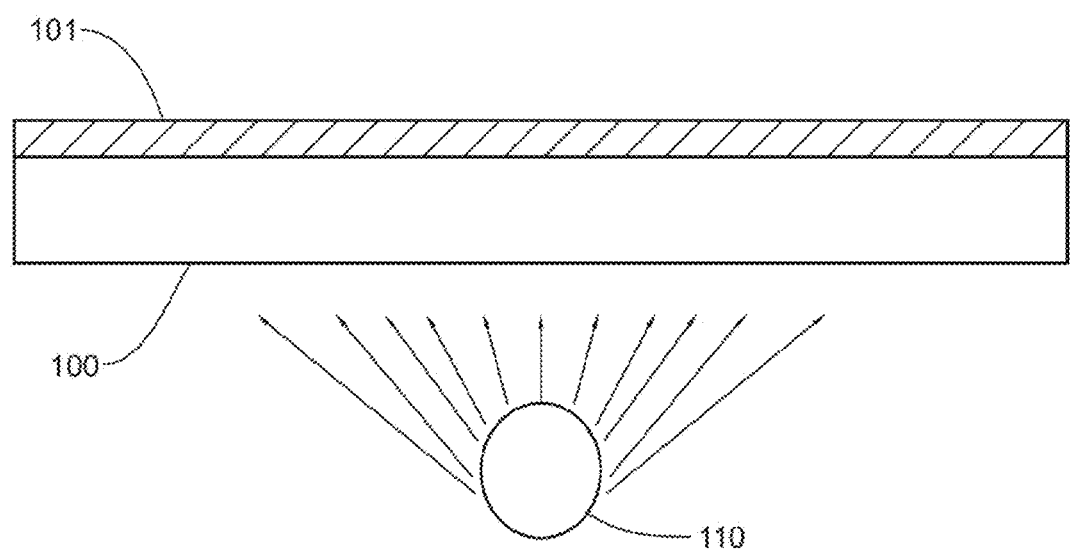

As shown in FIG. 6B, the first glass slide or PET block 100 and the thin transparent polyester film 101 undergo UV exposure to cure the UV epoxy. Preferably, a UV source 110 may radiate UV from a bottom side of the first glass slide or PET block 100. Thereby, the first glass slide or PET block 100 and the thin transparent polyester film 101 are bonded together at the first surface.

Figure 6C:
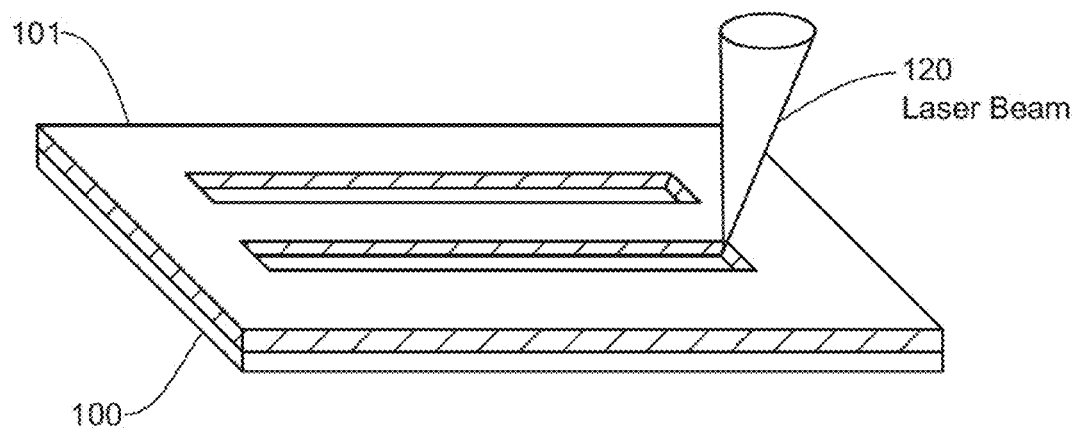
Figure 6D:
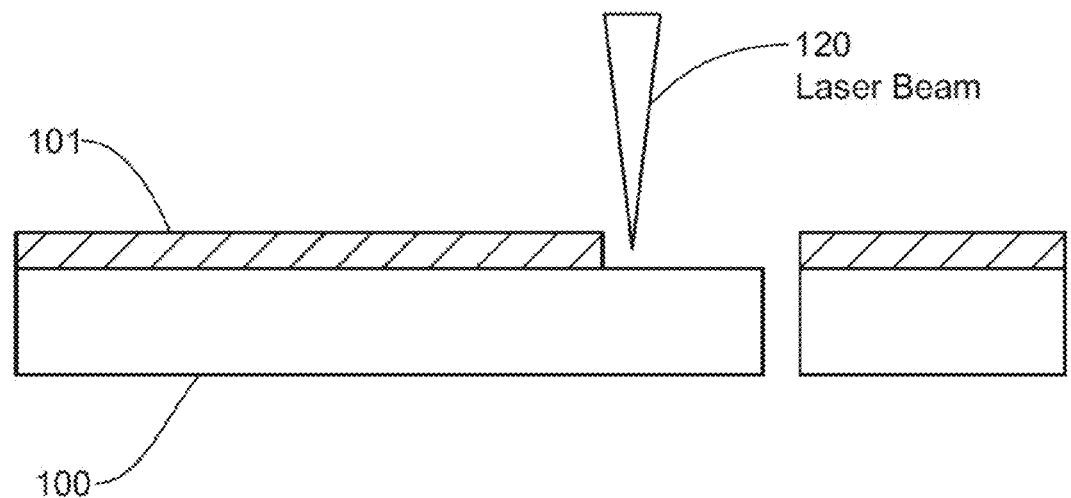

As shown in FIG. 6C, the thin transparent polyester film 101 is ablated to reflect a micro-channel design by using a laser beam 120. As shown in FIG. 6D, the laser beam 120 also may ablate through-holes in the first glass slide or PET block 100 to make an inlet or an outlet for the micro-channel(s). The laser beam 120 may be dynamically controlled by a microprocessor or an operator (not shown). In addition, the laser beam 120 may be adjusted in real-time to adjust the micro-channel design or to adopt a different micro-channel design.

Figure 6E:
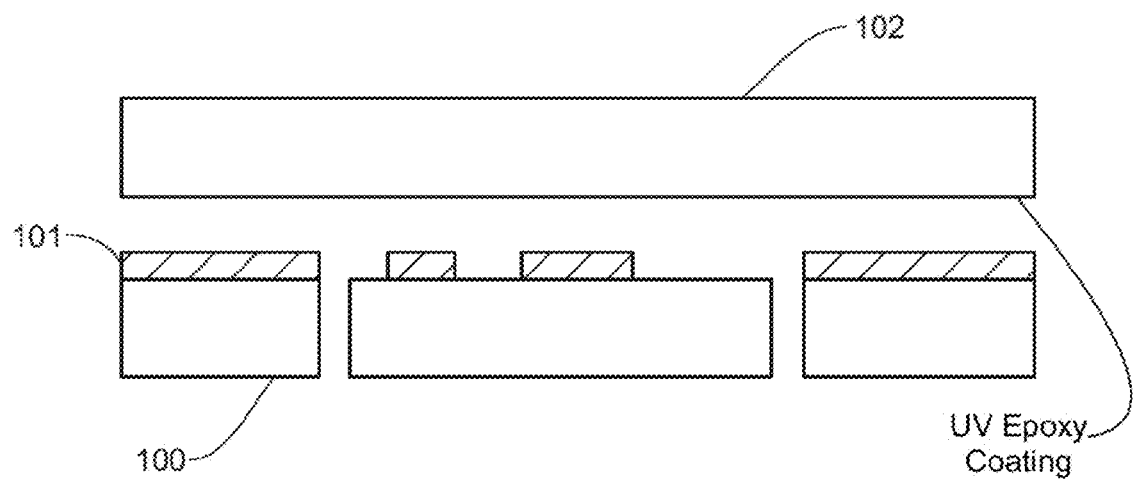

FIG. 6E shows a second glass slide or PET block 102 is place on the thin transparent polyester film 101. The second glass slide or PET block 102 may first undergo a cleaning step. A first surface of the second glass slide or PET 102 is coated with UV epoxy prior to being place on the thin transparent polyester film 101.

Figure 6F:
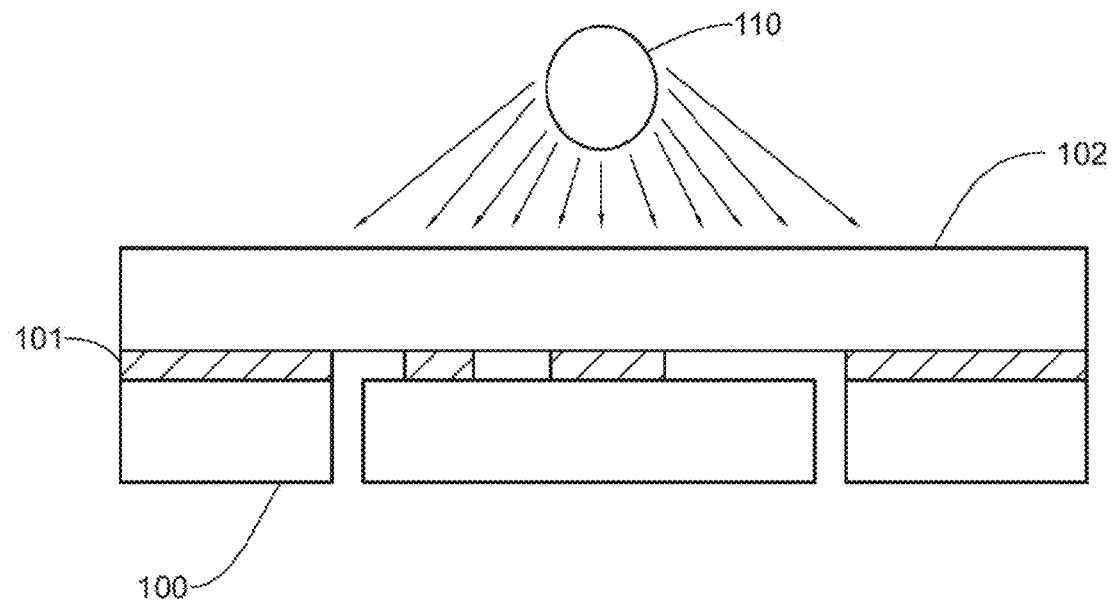

As shown in FIG. 6F, the second glass slide or PET block 102 while being on the thin transparent polyester film 101 undergoes UV exposure to cure the UV epoxy on its first surface. Preferably, the UV source or another UV source 110 may radiate UV from an upper side of the second glass slide or PET block 102. Thereby, the second glass slide or PET block 102 and the thin transparent polyester film 101 are bonded together at the first surface of the second glass slide or PET block 102 and the second surface of the thin transparent polyester film 101. The second glass slide or PET block 102 seals the micro-channel in the thin transparent polyester film 101.

Although not shown, the steps shown in FIG. 6A-6F may be repeated to form additional thin transparent films with micro-channels. For example, a second thin transparent film with a first surface coated with UV epoxy can be placed on the second glass slide or PET block 102 (shown in FIG. 6F). The second thin transparent film then undergoes UV exposure to cure UV epoxy and to be bonded to the second glass slide or PET block 102 (shown in FIG. 6). Laser beam is then introduced to ablate the second thin transparent film to form a second micro-channel. Laser beam also can ablate through the second glass slide or PET block 102, the first thin transparent film 101 and the first glass slide or PET block 100 (shown in FIG. 6F) to form an inlet and an outlet for the second micro-channel. Subsequently, a third glass slide or PET block with a first surface coated with UV epoxy can be placed on the second thin transparent polyester film. The third glass slide or PET block then undergoes UV exposure to cure UV epoxy and to bond the third glass slide or PET block to the second thin transparent polyester film. These steps can be repeated on additional thin transparent polyester films and glass slides or PET blocks to manufacture micro-channel in different thin transparent polyester films.

Figure 7:
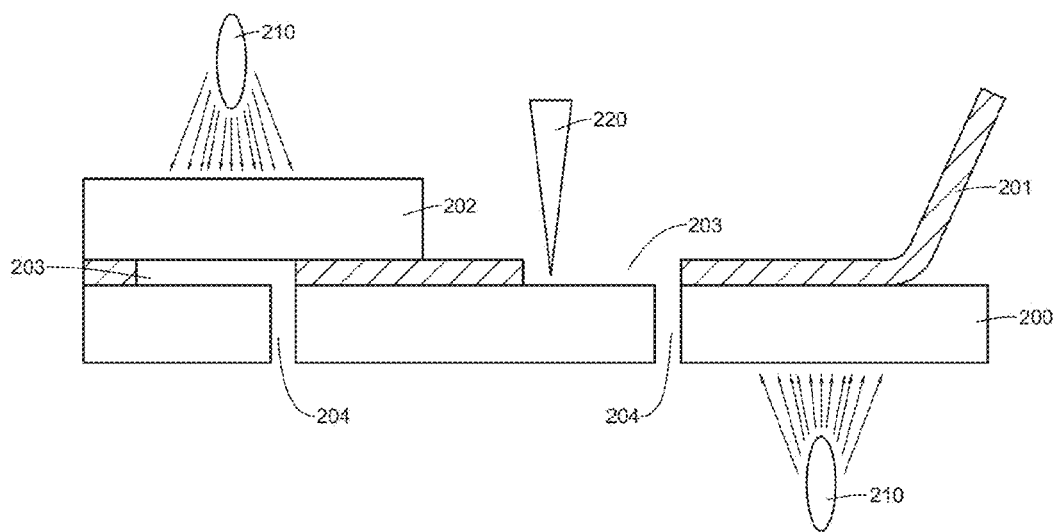
FIG. 7 illustrates a side view of the continuous manufacturing of a microfluidic chip according to an embodiment of the present invention.

FIG. 7 illustrates a side view of the continuous manufacturing of a microfluidic chip according to an embodiment of the present invention. As shown in FIG. 7, a first glass slide or PET block 200 is placed in a station. A thin transparent polyester film 201 having a first surface coated with UV epoxy is place on the first glass slide or PET block 200. A UV light source 210 radiates UV from a bottom side of the first glass slide or PET block 200. The UV epoxy on the first surface of the thin transparent polyester film 201 is cured, thereby bonding the first glass slide or PET block 200 and the thin film transparent polyester film 201. Then, a laser beam 220 is introduced to ablate the thin transparent polyester film 201 to form micro-channels 203.

The laser beam 220 may also ablate through-holes in the first glass slide or PET block 200 to form an inlet or an outlet 204 for the micro-channels. After micro-channels are formed, a second glass slide or PET block 202 having a first surface coated with UV epoxy is placed on the thin transparent polyester film 201. The UV light source or a second UV light source 210 radiates UV from an upper side of the second glass slide or PET block 202. The UV epoxy on the first surface of the second glass slide or PET block 202 is cured, thereby bonding the second glass slide or PET block 202 and the thin transparent polyester film 201.

As shown in FIG. 7, the method of manufacturing a microfluidic chip may be performed in a continuous manner. For example, the step of ablating the thin transparent polyester film 201 is performed immediately after the step of bonding the thin transparent polyester film 201 with the first glass slide or PET block 200.

Figure 8:
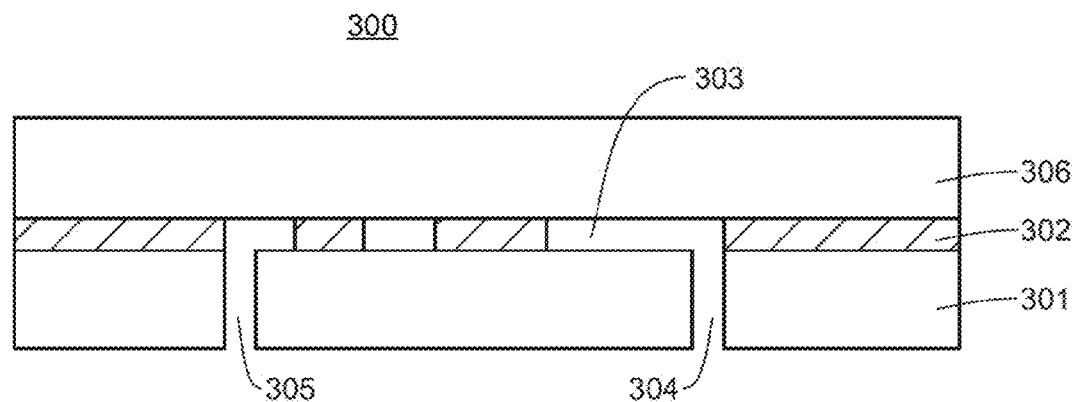
FIG. 8 is a side view of a microfluidic chip according to an embodiment of the present invention.

FIG. 8 is a side view of a microfluidic chip according to an embodiment of the present invention. As shown in FIG. 8, a microfluidic chip 300 includes a first glass slide or PET block 301, a thin transparent polyester film 302, micro-channel 303, an inlet 304 for the micro-channel 303, an outlet 305 for the micro-channel 303, and a second glass slide or PET block 306. In the microfluidic chip 300, the micro-channel 303 is solely in the thin transparent polyester film 302. The inlet 304 and the outlet 305 are through-holes in the first glass slide or PET block 301.

Although not shown, the first glass slide or PET block 301 is bonded to the thin transparent polyester film 302 using epoxy. Similarly, the second glass slide or PET block 306 is boned to another surface of the thin transparent polyester film 302 using epoxy. The epoxy may be UV curable.

Figure 9:
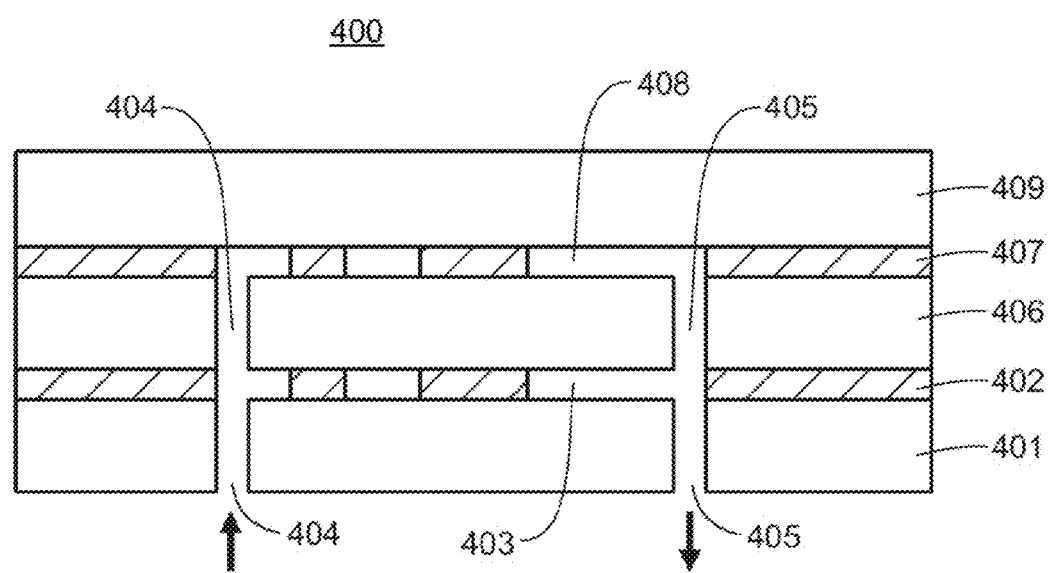
FIG. 9 is a side view of a multi-layer microfluidic chip according to an embodiment of the present invention.

FIG. 9 is a side view of a multi-layer microfluidic chip according to an embodiment of the present invention. As shown in FIG. 9, a microfluidic chip 400 may be a multi-layer microfluidic chip. The microfluidic chip 400 includes a first glass slide or PET block 401, a first thin transparent polyester film 402, a first micro-channel 403, an inlet 404 for the micro-channel 403, an outlet 405 for the micro-channel 403, and a second glass slide or PET block 406. The micro-channel 403 is in the first thin transparent polyester film 402. The inlet 404 and the outlet 405 are through-holes in the first glass slide or PET block 401.

The microfluidic chip 400 further includes a second thin transparent polyester film 407 on the second glass slide or PET block 406, and a second micro-channel 408 in the second thin transparent polyester film 407. The microfluidic chip 400 also includes a third glass slide or PET block 409. The inlet 404 and the outlet 405 also can be through the second glass slide or PET block 406. Alternatively, another set of inlet and outlet (not shown) may be only for the second micro-channel 408 and are separate through-holes in the first glass slide or PET block 401, the first thin transparent polyester film 402, the second glass slide or PET block 406 and the second thin transparent polyester film 407.

Although not shown, the first glass slide or PET block 401 is bonded to the first thin transparent polyester film 402 using epoxy. The second glass slide or PET block 406 is boned to the first thin transparent polyester film 402 and the second thin transparent polyester film 407 using epoxy. The third glass slide or PET block 409 is bonded to the second thin transparent polyester film 407 using epoxy. The epoxy may be UV curable.

Although two micro-channels in two polyester films are illustrated, any number of micro-channels in different layers may be implemented. The method of manufacturing microfluidic chips according to an embodiment of the present invention provides a method of continuously forming micro-channels in chips. The method of manufacturing microfluidic chips according to an embodiment of the present invention provides a method of manufacturing that can reliably and quickly form micro-channels in chips.

In addition, microfluidic chips according to an embodiment of the present invention includes micro-channel in a thin biaxially-oriented polyethylene terephthalate ("BoPET") film. The PET film may be Mylar or another transparent, stable, and electrical insulative film.

Further, the method of manufacturing microfluidic chips according to an embodiment of the present invention employs dynamically controlled laser beam to ablate a thin transparent polyester film to provide real-time adjustment of laser beam/channel design.

It will be apparent to those skilled in the art that various modifications and variations can be made in the method of manufacturing microfluidic chips and the microfluidic chips of embodiments of the invention without departing from the spirit or scope of the invention. Thus, it is intended that embodiments of the invention cover the modifications and variations of this invention provided they come within the scope of the appended claims and their equivalents.

What is claimed:

1. A method for manufacturing a device, comprising:
   coating UV epoxy on a first side of a BoPET film;
   placing the BoPET film with UV epoxy coated thereon on a first substrate with the first side facing the first substrate;
   curing the UV epoxy on the first side of the BoPET film to attach the BoPET film on the first substrate;
   forming at least one microfluidic pathway in the BoPET film that is attached on the first substrate;
   coating UV epoxy on a first side of a second substrate;
   placing the second substrate on the BoPET film with the first side of the second substrate facing a second side of the BoPET film; and
   curing the UV epoxy on the first side of the second substrate to attach the BoPET film that includes the microfluidic pathway formed therein to the second substrate.

2. The method according to claim 1, wherein the step of forming the at least one microfluidic pathway includes applying a laser beam to ablate the first substrate.

3. The method according to claim 1, further comprising the step of forming an inlet by applying a laser beam to ablate the first substrate.

4. The method according to claim 3, wherein the step of forming an inlet is performed prior to placing the second substrate on the BoPET film.

5. The method according to claim 1, wherein the first and second substrates are glass substrates.

6. The method according to claim 1, further comprising:
   coating UV epoxy on a first side of a second BoPET film;
   placing the second BoPET film on the second substrate with the first side of the second BoPET film facing the second substrate;
   curing the UV epoxy on the first side of the second BoPET film to attach the second BoPET film on the second substrate;
   forming at least one microfluidic pathway in the second BoPET film;
   coating UV epoxy on a first side of a third substrate;
   placing the third substrate on the second BoPET film with the first side of the second substrate facing a second side of the BoPET film; and
   curing the UV epoxy on the first side of the third substrate to attach the second BoPET film to the third substrate.

7. The method according to claim 6, wherein the step of forming the at least one microfluidic pathway includes applying a laser beam to ablate the first substrate.

8. The method according to claim 6, further comprising the step of forming an inlet by applying a laser beam to ablate at least one of the first substrate and the second substrate.

9. The method according to claim 8, wherein the step of forming an inlet is performed prior to placing the third substrate on the second BoPET film.

10. The method according to claim 6, wherein the first, second and third substrates are glass substrates.

11. The method according to claim 1, wherein the steps are performed continuously.

12. A microfluidic chip manufactured using the method according to claim 1.

13. A microfluidic chip, comprising:
   a first substrate; a BoPET film bonded on the first substrate, where an at least one microfluidic pathway is formed in the BoPET film, wherein said BoPET film is coated with an UV epoxy; and
   a second substrate bonded on the BoPET film, wherein the microfluidic pathway is formed without using a mold, and wherein the second substrate is configured to be bonded on the BoPET film after the microfluidic pathway is formed in the BoPET film.

14. The microfluidic chip according to claim 13, wherein the at least one microfluidic pathway is formed by applying laser beam to ablating the BoPET film prior to the second substrate bonded on the BoPET film.

15. The microfluidic chip according to claim 13, further comprising an inlet in the first substrate, the inlet formed by applying laser beam to ablating the first substrate.

16. The microfluidic chip according to claim 13, wherein the first and second substrates are glass substrates.

17. The microfluidic chip according to claim 13, further comprising:
   a second BoPET film bonded on the second substrate, wherein an at least one microfluidic pathway is formed in the second BoPET film; and
   a third substrate bonded on the second BoPET film.

18. The microfluidic chip according to claim 17, wherein the at least one microfluidic pathway in the second BoPET film is formed by applying a laser beam, wherein said laser beam is configured to ablate the second BoPET film prior to the third substrate being bonded on the second BoPET film.

19. The microfluidic chip according to claim 17, further comprising an inlet in at least one of the first substrate and the second substrate.

20. The microfluidic chip according to claim 13, wherein the first, second and third substrates are glass substrates.

* * * * *